United States Patent
Dirac et al.

(10) Patent No.: US 11,020,526 B2
(45) Date of Patent: Jun. 1, 2021

(54) SPRINKLER CANNULA

(75) Inventors: Holger Dirac, Birkerød (DK); John Myhre Frederiksen, Borup (DK); Søren Thorup, Frederiksberg C (DK); Bo L. Justesen, Ringsted (DK)

(73) Assignee: Unomedical A/S, Birkerød (DK)

( * ) Notice: Subject to any disclaimer, the term of this patent is extended or adjusted under 35 U.S.C. 154(b) by 0 days.

(21) Appl. No.: 13/823,236

(22) PCT Filed: Sep. 30, 2011

(86) PCT No.: PCT/EP2011/067066
§ 371 (c)(1),
(2), (4) Date: Jun. 10, 2013

(87) PCT Pub. No.: WO2012/045667
PCT Pub. Date: Apr. 12, 2012

(65) Prior Publication Data
US 2013/0245555 A1 Sep. 19, 2013

Related U.S. Application Data

(60) Provisional application No. 61/389,595, filed on Oct. 4, 2010.

(30) Foreign Application Priority Data

Oct. 4, 2010 (EP) .................... 10186437

(51) Int. Cl.
*A61M 5/158* (2006.01)
*A61M 5/32* (2006.01)
(Continued)

(52) U.S. Cl.
CPC .......... *A61M 5/158* (2013.01); *A61M 5/3291* (2013.01); *A61M 25/007* (2013.01);
(Continued)

(58) Field of Classification Search
CPC ...... A61M 5/14; A61M 5/158; A61M 5/3291; A61M 2025/0081; A61M 2025/0253
(Continued)

(56) References Cited

U.S. PATENT DOCUMENTS

| 1,592,462 A | 7/1926 | MacGregor |
| 2,047,010 A | 7/1936 | Dickinson |

(Continued)

FOREIGN PATENT DOCUMENTS

| DE | 4 342 329 A1 | 6/1994 |
| DE | 196 31 921 A1 | 3/1997 |

(Continued)

OTHER PUBLICATIONS

International Search Report completed Jun. 27, 2012 for International Application No. PCT/EP2011/067066.
(Continued)

*Primary Examiner* — Manuel A Mendez
*Assistant Examiner* — Justin L Zamory
(74) *Attorney, Agent, or Firm* — Taft Stettinius & Hollister LLP; Ryan O. White; Derek B. Lavender (57) ABSTRACT

An infusion device (50) incl. a preferably soft cannula (1) configured to be inserted by means of an insertion needle. The cannula has a tubular body member having a proximal end and a subcutaneously placed distal portion having a distal end where the distal portion is provided with an opening (2) allowing a portion of a drug conveyed through the tubular body member to discharge. The cannula further comprise, in the distal portion, a radial opening allowing a portion of a drug conveyed through the tubular body member to discharge.

14 Claims, 6 Drawing Sheets

(51) Int. Cl.
  *A61M 25/00* (2006.01)
  *A61M 5/142* (2006.01)
(52) U.S. Cl.
  CPC .............. *A61M 25/0015* (2013.01); *A61M 2005/14252* (2013.01); *A61M 2005/1586* (2013.01)
(58) Field of Classification Search
  USPC ............................ 604/117, 151, 174, 272
  See application file for complete search history.

(56) References Cited

U.S. PATENT DOCUMENTS

| | | |
|---|---|---|
| 2,295,849 A | 9/1942 | Kayden |
| 2,690,529 A | 9/1954 | Lindblad |
| 2,972,779 A | 2/1961 | Cowley |
| 3,059,802 A | 10/1962 | Mitchell |
| 3,074,541 A | 1/1963 | Roehr |
| 3,149,186 A | 9/1964 | Coanda |
| 3,221,739 A | 12/1965 | Rosenthal |
| 3,221,740 A | 12/1965 | Rosenthal |
| 3,306,291 A | 2/1967 | Burke |
| 3,485,352 A | 12/1969 | Pilger |
| 3,509,879 A | 5/1970 | Bathish et al. |
| 3,519,158 A | 7/1970 | Anderson |
| 3,547,119 A | 12/1970 | Hall et al. |
| 3,575,337 A | 4/1971 | Bernhardt |
| 3,610,240 A | 10/1971 | Harautuneian |
| 3,615,039 A | 10/1971 | Ward |
| 3,670,727 A | 6/1972 | Reiterman |
| 3,783,895 A | 1/1974 | Weichselbaum |
| 3,788,374 A | 1/1974 | Saijo |
| 3,810,469 A | 5/1974 | Hurschman |
| 3,835,862 A | 9/1974 | Villari |
| 3,840,011 A | 10/1974 | Wright |
| 3,893,448 A | 7/1975 | Brantigan |
| 3,937,219 A | 2/1976 | Karakashian |
| 3,986,507 A | 10/1976 | Watt |
| 3,986,508 A | 10/1976 | Barrington |
| 3,995,518 A | 12/1976 | Spiroff |
| 4,022,205 A | 5/1977 | Tenczar |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,296,786 A | 10/1981 | Brignola |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,378,015 A | 3/1983 | Wardlaw |
| 4,402,407 A | 9/1983 | Maly |
| 4,415,393 A | 11/1983 | Grimes |
| 4,417,886 A | 11/1983 | Frankhouser et al. |
| 4,464,178 A | 8/1984 | Dalton |
| 4,473,369 A | 9/1984 | Lueders et al. |
| 4,484,910 A | 11/1984 | Sarnoff et al. |
| 4,500,312 A | 2/1985 | McFarlane |
| 4,508,367 A | 4/1985 | Oreopoulos et al. |
| 4,525,157 A | 6/1985 | Vaillancourt |
| 4,530,695 A | 7/1985 | Phillips et al. |
| 4,531,937 A | 7/1985 | Yates |
| 4,543,088 A | 9/1985 | Bootman et al. |
| 4,563,177 A | 1/1986 | Kamen |
| 4,610,469 A | 9/1986 | Wolff-Mooij |
| 4,617,019 A | 10/1986 | Fecht |
| 4,713,059 A | 12/1987 | Bickelhaupt et al. |
| 4,734,092 A | 3/1988 | Millerd |
| 4,755,173 A | 7/1988 | Konopka et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A | 1/1990 | Miskinyar |
| 4,895,570 A | 1/1990 | Larkin |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,956,989 A | 9/1990 | Nakajima |
| 4,970,954 A | 11/1990 | Weir et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olson |
| 5,020,665 A | 6/1991 | Bruno |
| 5,024,662 A | 6/1991 | Menes et al. |
| 5,067,496 A | 11/1991 | Eisele |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van den Haak |
| 5,116,325 A | 5/1992 | Paterson |
| 5,121,751 A | 6/1992 | Panalletta |
| 5,129,884 A | 7/1992 | Dysarz |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,375 A | 9/1992 | Sullivan et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,248,301 A | 9/1993 | Koenig et al. |
| 5,256,149 A | 10/1993 | Banik et al. |
| 5,256,152 A | 10/1993 | Marks |
| 5,257,980 A | 11/1993 | Van Antwerp et al. |
| 5,267,963 A | 12/1993 | Bachynsky |
| 5,267,979 A | 12/1993 | Appling et al. |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,344,007 A | 9/1994 | Nakamura et al. |
| 5,350,392 A | 9/1994 | Purcell et al. |
| 5,354,280 A | 10/1994 | Haber et al. |
| 5,354,337 A | 10/1994 | Hoy |
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,379,895 A | 1/1995 | Foslien |
| 5,380,307 A * | 1/1995 | Chee et al. .................. 604/264 |
| 5,384,174 A | 1/1995 | Ward et al. |
| 5,387,197 A | 2/1995 | Smith et al. |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,425,715 A | 6/1995 | Dalling et al. |

(56) References Cited

U.S. PATENT DOCUMENTS

| | | | |
|---|---|---|---|
| 5,429,607 | A | 7/1995 | McPhee |
| 5,429,613 | A | 7/1995 | D'Amico |
| 5,439,473 | A | 8/1995 | Jorgensen |
| D362,718 | S | 9/1995 | Deily et al. |
| 5,449,349 | A | 9/1995 | Sallee et al. |
| 5,451,210 | A | 9/1995 | Kramer et al. |
| 5,478,316 | A | 12/1995 | Bitdinger et al. |
| 5,490,841 | A | 2/1996 | Landis |
| 5,501,675 | A | 3/1996 | Erskine |
| 5,505,709 | A | 4/1996 | Funderburk et al. |
| 5,507,730 | A | 4/1996 | Haber et al. |
| 5,514,117 | A | 5/1996 | Lynn |
| 5,520,654 | A | 5/1996 | Wahlberg |
| 5,522,803 | A | 6/1996 | Teissen-Simony |
| 5,527,287 | A | 6/1996 | Miskinyar et al. |
| 5,533,974 | A | 7/1996 | Gaba |
| 5,540,709 | A | 7/1996 | Ramel |
| 5,545,143 | A | 8/1996 | Fischell |
| 5,545,152 | A | 8/1996 | Funderburk et al. |
| 5,549,577 | A | 8/1996 | Siegel et al. |
| 5,554,130 | A | 9/1996 | McDonald et al. |
| 5,558,650 | A | 9/1996 | McPhee |
| 5,562,629 | A | 10/1996 | Haughton et al. |
| 5,562,636 | A | 10/1996 | Utterberg |
| 5,573,510 | A | 11/1996 | Isaacson |
| 5,575,777 | A | 11/1996 | Cover et al. |
| 5,584,813 | A | 12/1996 | Livingston et al. |
| 5,586,553 | A | 12/1996 | Halili et al. |
| 5,591,188 | A | 1/1997 | Waisman |
| 5,599,309 | A | 2/1997 | Marshall et al. |
| 5,599,315 | A | 2/1997 | McPhee |
| 5,599,318 | A | 2/1997 | Sweeney et al. |
| 5,628,765 | A | 5/1997 | Morita |
| 5,643,214 | A | 7/1997 | Marshall |
| 5,643,216 | A | 7/1997 | White |
| 5,643,220 | A | 7/1997 | Cosme |
| 5,658,256 | A | 8/1997 | Shields |
| 5,662,617 | A | 9/1997 | Odell et al. |
| 5,665,071 | A | 9/1997 | Wyrick |
| 5,665,075 | A | 9/1997 | Gyure et al. |
| 5,676,156 | A | 10/1997 | Yoon |
| 5,681,323 | A | 10/1997 | Arick |
| 5,695,476 | A | 12/1997 | Harris |
| 5,697,907 | A | 12/1997 | Gaba |
| 5,700,250 | A | 12/1997 | Erskine |
| 5,702,371 | A | 12/1997 | Bierman |
| 5,704,920 | A | 1/1998 | Gyure |
| 5,709,662 | A | 1/1998 | Olive et al. |
| 5,714,225 | A | 2/1998 | Hansen et al. |
| 5,738,641 | A | 4/1998 | Watson et al. |
| 5,741,288 | A | 4/1998 | Rife |
| 5,752,923 | A | 5/1998 | Terwilliger |
| 5,807,316 | A | 9/1998 | Teeple |
| 5,807,348 | A | 9/1998 | Zinger et al. |
| 5,810,835 | A | 9/1998 | Ryan et al. |
| 5,817,058 | A | 10/1998 | Shaw |
| 5,820,598 | A | 10/1998 | Gazza et al. |
| 5,827,236 | A | 10/1998 | Takahashi |
| 5,833,666 | A | 11/1998 | Davis et al. |
| 5,843,001 | A | 12/1998 | Goldenberg |
| 5,848,990 | A | 12/1998 | Cirelli et al. |
| 5,851,197 | A | 12/1998 | Marano et al. |
| 5,858,001 | A | 1/1999 | Tsals et al. |
| 5,865,806 | A | 2/1999 | Howell |
| 5,899,886 | A | 5/1999 | Cosme |
| 5,911,705 | A | 6/1999 | Howell |
| 5,913,846 | A | 6/1999 | Szabo |
| 5,916,199 | A | 6/1999 | Miles |
| 5,919,167 | A | 7/1999 | Mulhauser et al. |
| 5,919,170 | A | 7/1999 | Woessner |
| 5,925,032 | A | 7/1999 | Clements |
| 5,935,109 | A | 8/1999 | Donnan |
| 5,947,931 | A | 9/1999 | Bierman |
| 5,947,935 | A | 9/1999 | Rhinehart et al. |
| 5,951,523 | A | 9/1999 | Osterlind et al. |
| 5,954,643 | A | 9/1999 | VanAntwerp et al. |
| 5,957,892 | A | 9/1999 | Thorne |
| 5,957,897 | A | 9/1999 | Jeffrey |
| 5,968,011 | A | 10/1999 | Larsen et al. |
| 5,971,966 | A | 10/1999 | Lav |
| 5,975,120 | A | 11/1999 | Novosel |
| 5,980,488 | A | 11/1999 | Thorne |
| 5,980,506 | A | 11/1999 | Mathiasen |
| 5,984,224 | A | 11/1999 | Yang |
| 5,984,897 | A | 11/1999 | Petersen et al. |
| D417,733 | S | 12/1999 | Howell et al. |
| 6,017,328 | A | 1/2000 | Fischell et al. |
| 6,017,598 | A | 1/2000 | Kreischer et al. |
| D421,119 | S | 2/2000 | Musgrave et al. |
| 6,024,727 | A | 2/2000 | Thorne et al. |
| 6,039,629 | A | 3/2000 | Mitchell |
| 6,042,570 | A | 3/2000 | Bell et al. |
| 6,045,533 | A | 4/2000 | Kriesel et al. |
| 6,045,534 | A | 4/2000 | Jacobsen et al. |
| 6,050,976 | A | 4/2000 | Thorne et al. |
| 6,053,893 | A | 4/2000 | Bucher |
| 6,053,930 | A | 4/2000 | Ruppert |
| 6,056,718 | A | 5/2000 | Funderburk et al. |
| 6,056,726 | A | 5/2000 | Isaacson |
| 6,074,369 | A | 6/2000 | Sage et al. |
| 6,074,371 | A | 6/2000 | Fischell |
| 6,077,244 | A | 6/2000 | Botich et al. |
| 6,079,432 | A | 6/2000 | Paradis |
| 6,086,008 | A | 7/2000 | Gray et al. |
| 6,086,575 | A | 7/2000 | Mejslov |
| 6,090,068 | A | 7/2000 | Chanut |
| 6,093,172 | A | 7/2000 | Funderburk et al. |
| 6,093,179 | A | 7/2000 | O'Hara et al. |
| 6,099,503 | A | 8/2000 | Stradella |
| 6,105,218 | A | 8/2000 | Reekie |
| 6,106,498 | A | 8/2000 | Friedli et al. |
| 6,120,482 | A | 9/2000 | Szabo |
| 6,123,690 | A | 9/2000 | Mejslov |
| 6,132,755 | A | 10/2000 | Eicher et al. |
| 6,139,534 | A | 10/2000 | Niedospial, Jr. |
| 6,159,181 | A | 12/2000 | Crossman et al. |
| 6,183,464 | B1 | 2/2001 | Sharp et al. |
| 6,191,338 | B1 | 2/2001 | Haller |
| 6,193,694 | B1 | 2/2001 | Bell et al. |
| 6,210,420 | B1 | 4/2001 | Mauze et al. |
| 6,219,574 | B1 | 4/2001 | Cormier et al. |
| 6,221,058 | B1 | 4/2001 | Kao et al. |
| 6,248,093 | B1 | 6/2001 | Moberg |
| 6,261,272 | B1 | 7/2001 | Gross et al. |
| 6,280,434 | B1 * | 8/2001 | Kinoshita ......... A61M 25/0041 600/435 |
| 6,293,925 | B1 | 9/2001 | Safabash et al. |
| 6,302,866 | B1 | 10/2001 | Marggi |
| 6,319,232 | B1 | 11/2001 | Kashmer |
| 6,322,535 | B1 | 11/2001 | Hitchins et al. |
| 6,322,808 | B1 | 11/2001 | Trautman et al. |
| 6,334,856 | B1 | 1/2002 | Allen et al. |
| 6,355,021 | B1 | 3/2002 | Nielsen et al. |
| 6,364,113 | B1 | 4/2002 | Faasse et al. |
| 6,378,218 | B2 | 4/2002 | Sigwart et al. |
| 6,379,335 | B1 | 4/2002 | Rigon et al. |
| 6,387,076 | B1 | 5/2002 | Van Landuyt |
| 6,387,078 | B1 | 5/2002 | Gillespie, III |
| 6,405,876 | B1 | 6/2002 | Seshimoto et al. |
| 6,440,096 | B1 | 8/2002 | Lastovich et al. |
| 6,447,482 | B1 | 9/2002 | Rønborg et al. |
| 6,450,992 | B1 | 9/2002 | Cassidy, Jr. |
| 6,485,461 | B1 | 11/2002 | Mason et al. |
| 6,488,663 | B1 | 12/2002 | Steg |
| 6,503,222 | B2 | 1/2003 | Lo |
| 6,517,517 | B1 | 2/2003 | Farrugia et al. |
| 6,517,521 | B1 | 2/2003 | Ly |
| 6,520,938 | B1 | 2/2003 | Funderburk et al. |
| D472,316 | S | 3/2003 | Douglas et al. |
| 6,533,763 | B1 * | 3/2003 | Schneiter ............ A61M 25/007 604/264 |
| D472,630 | S | 4/2003 | Douglas et al. |
| 6,572,586 | B1 | 6/2003 | Wojcik |
| 6,579,267 | B2 | 6/2003 | Lynch et al. |

(56) References Cited

U.S. PATENT DOCUMENTS

| | | |
|---|---|---|
| 6,582,397 B2 | 6/2003 | Alesi et al. |
| 6,595,962 B1 | 7/2003 | Perthu |
| 6,607,509 B2 | 8/2003 | Bobroff et al. |
| 6,607,511 B2 | 8/2003 | Halseth et al. |
| 6,613,064 B2 | 9/2003 | Rutynowski et al. |
| 6,620,133 B1 | 9/2003 | Steck |
| 6,620,136 B1 | 9/2003 | Pressly, Sr. et al. |
| 6,620,140 B1 | 9/2003 | Metzger |
| 6,629,949 B1 | 10/2003 | Douglas |
| 6,645,181 B1 | 11/2003 | Lavi et al. |
| 6,645,182 B1 | 11/2003 | Szabo |
| 6,659,982 B2 | 12/2003 | Douglas et al. |
| 6,685,674 B2 | 2/2004 | Douglas et al. |
| 6,689,118 B2 * | 2/2004 | Alohas et al. ............ 604/506 |
| 6,699,218 B2 | 3/2004 | Flaherty et al. |
| 6,702,779 B2 | 3/2004 | Connelly et al. |
| 6,726,649 B2 | 4/2004 | Swenson et al. |
| 6,736,797 B1 | 5/2004 | Larsen et al. |
| 6,743,203 B1 | 6/2004 | Pickhard |
| 6,749,587 B2 | 6/2004 | Flaherty |
| 6,749,589 B1 | 6/2004 | Douglas et al. |
| 6,755,805 B1 | 6/2004 | Reid |
| 6,776,775 B1 | 8/2004 | Mohammad |
| 6,790,199 B1 | 9/2004 | Gianakos |
| 6,805,686 B1 | 10/2004 | Fathallah et al. |
| 6,808,506 B2 | 10/2004 | Lastovich et al. |
| 6,811,545 B2 | 11/2004 | Vaillancourt |
| 6,814,720 B2 | 11/2004 | Olsen et al. |
| 6,824,530 B2 | 11/2004 | Wagner et al. |
| 6,824,531 B1 | 11/2004 | Zecha, Jr. et al. |
| 6,830,562 B2 | 12/2004 | Mogensen et al. |
| 6,837,877 B2 | 1/2005 | Zurcher |
| 6,837,878 B2 | 1/2005 | Smutney et al. |
| 6,840,922 B2 | 1/2005 | Nielsen et al. |
| 6,880,701 B2 | 4/2005 | Bergeron et al. |
| 6,923,791 B2 | 8/2005 | Douglas |
| 6,926,694 B2 | 8/2005 | Marano-Ford et al. |
| 6,939,324 B2 | 9/2005 | Gonnelli et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkinson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkinson et al. |
| 7,115,112 B2 | 10/2006 | Mogensen et al. |
| 7,137,968 B1 | 11/2006 | Burrell et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow, Jr. |
| 7,322,473 B2 | 1/2008 | Fux |
| 7,407,491 B2 | 8/2008 | Fangrow, Jr. |
| 7,407,493 B2 | 8/2008 | Cane' |
| 7,431,876 B2 | 10/2008 | Mejlhede et al. |
| 7,441,655 B1 | 10/2008 | Hoftman |
| 7,569,262 B2 | 8/2009 | Szabo et al. |
| 7,648,494 B2 | 1/2010 | Kornerup et al. |
| 7,766,867 B2 | 8/2010 | Lynch et al. |
| 7,846,132 B2 | 12/2010 | Gravesen et al. |
| 7,850,652 B2 | 12/2010 | Liniger et al. |
| 8,012,126 B2 | 9/2011 | Tipsmark et al. |
| 8,087,333 B2 | 1/2012 | Oishi |
| 8,123,724 B2 | 2/2012 | Gillespie, III |
| 8,303,549 B2 | 11/2012 | Mejlhede et al. |
| 8,323,250 B2 | 12/2012 | Chong et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer |
| 2001/0053889 A1 | 12/2001 | Marggi |
| 2001/0056284 A1 | 12/2001 | Purcell et al. |
| 2002/0022798 A1 | 2/2002 | Connelly et al. |
| 2002/0022855 A1 | 2/2002 | Bobroff et al. |
| 2002/0026152 A1 | 2/2002 | Bierman |
| 2002/0055711 A1 | 5/2002 | Lavi et al. |
| 2002/0068904 A1 | 6/2002 | Bierman et al. |
| 2002/0072720 A1 | 6/2002 | Hague et al. |
| 2002/0074345 A1 | 6/2002 | Schneider et al. |
| 2002/0077599 A1 | 6/2002 | Wojcik |
| 2002/0082543 A1 | 6/2002 | Park et al. |
| 2002/0095138 A1 | 7/2002 | Lynch et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Ackley et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0030220 A1 * | 2/2004 | Hamm ............ 600/156 |
| 2004/0044306 A1 | 3/2004 | Lynch et al. |

(56) References Cited

U.S. PATENT DOCUMENTS

| | | |
|---|---|---|
| 2004/0049159 A1 | 3/2004 | Barrus et al. |
| 2004/0055711 A1 | 3/2004 | Martin et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0162521 A1 | 8/2004 | Bengtsson |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty et al. |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Kornerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Butikofer et al. |
| 2006/0015076 A1 | 1/2006 | Heinzerling et al. |
| 2006/0030815 A1 | 2/2006 | Csincsura et al. |
| 2006/0036214 A1 | 2/2006 | Mogensen et al. |
| 2006/0041224 A1 | 2/2006 | Jensen |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld |
| 2006/0142698 A1 | 6/2006 | Ethelfeld |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney, II et al. |
| 2006/0184140 A1 | 8/2006 | Okiyama |
| 2006/0200073 A1 | 9/2006 | Radmer et al. |
| 2006/0241551 A1 | 10/2006 | Lynch et al. |
| 2006/0247553 A1 | 11/2006 | Diermann et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1 | 11/2006 | Nielsen et al. |
| 2006/0264890 A1 | 11/2006 | Moberg et al. |
| 2007/0005017 A1 | 1/2007 | Alchas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049865 A1 | 3/2007 | Radmer et al. |
| 2007/0049870 A1 | 3/2007 | Gray et al. |
| 2007/0051784 A1 | 3/2007 | Money et al. |
| 2007/0066955 A1 | 3/2007 | Sparholt et al. |
| 2007/0066958 A1 | 3/2007 | Wright |
| 2007/0088271 A1 | 4/2007 | Richards et al. |
| 2007/0093754 A1 | 4/2007 | Mogensen et al. |
| 2007/0104596 A1 | 5/2007 | Preuthun et al. |
| 2007/0112301 A1 | 5/2007 | Preuthun et al. |
| 2007/0112303 A1 | 5/2007 | Liniger |
| 2007/0129688 A1 | 6/2007 | Scheurer et al. |
| 2007/0129691 A1 | 6/2007 | Sage, Jr. et al. |
| 2007/0173767 A1 | 7/2007 | Lynch et al. |
| 2007/0191772 A1 | 8/2007 | Wojcik |
| 2007/0191773 A1 | 8/2007 | Wojcik |
| 2007/0203454 A1 | 8/2007 | Shermer et al. |
| 2007/0185441 A1 | 9/2007 | Fangrow, Jr. |
| 2007/0213673 A1 | 9/2007 | Douglas |
| 2007/0179444 A1 | 10/2007 | Causey et al. |
| 2007/0244448 A1 | 10/2007 | Lastovich et al. |
| 2007/0282269 A1 | 12/2007 | Carter et al. |
| 2007/0299409 A1 | 12/2007 | Whitbourne et al. |
| 2008/0021375 A1* | 1/2008 | Burns .............. A61M 5/31526 604/27 |
| 2008/0058692 A1 | 3/2008 | Propp et al. |
| 2008/0119707 A1 | 5/2008 | Stafford |
| 2008/0200897 A1 | 8/2008 | Hoss et al. |
| 2008/0269687 A1 | 10/2008 | Chong |
| 2008/0312601 A1 | 12/2008 | Cane' |
| 2009/0062767 A1 | 3/2009 | Van Antwerp et al. |
| 2009/0118592 A1 | 5/2009 | Klitgaard |
| 2009/0326456 A1 | 12/2009 | Cross et al. |
| 2010/0004597 A1 | 1/2010 | Gyrn et al. |
| 2010/0022956 A1 | 1/2010 | Tipsmark et al. |
| 2010/0137829 A1 | 6/2010 | Nielsen et al. |
| 2010/0228226 A1 | 9/2010 | Nielsen |
| 2010/0262078 A1 | 10/2010 | Blomquist |
| 2011/0054399 A1 | 3/2011 | Chong et al. |
| 2013/0024555 A1 | 1/2013 | Bartfai-Walcott et al. |

FOREIGN PATENT DOCUMENTS

| | | |
|---|---|---|
| DE | 299 05 072 U1 | 9/1999 |
| DE | 101 17 285 A1 | 11/2002 |
| DE | 203 20 207 U1 | 11/2004 |
| EP | 0117632 B1 | 9/1984 |
| EP | 0239244 B1 | 2/1987 |
| EP | 0272530 A2 | 6/1988 |
| EP | 0451040 A1 | 10/1991 |
| EP | 0544837 B1 | 6/1993 |
| EP | 0615768 A2 | 9/1994 |
| EP | 0651662 B1 | 5/1995 |
| EP | 0652027 A1 | 5/1995 |
| EP | 0657184 A1 | 6/1995 |
| EP | 0688232 B1 | 12/1995 |

(56) References Cited

FOREIGN PATENT DOCUMENTS

| | | |
|---|---|---|
| EP | 0714631 B1 | 6/1996 |
| EP | 0744183 A2 | 11/1996 |
| EP | 0747006 A1 | 12/1996 |
| EP | 0775501 B1 | 5/1997 |
| EP | 0799626 A1 | 10/1997 |
| EP | 0937475 A2 | 8/1999 |
| EP | 0956879 A1 | 11/1999 |
| EP | 1086718 A1 | 3/2001 |
| EP | 1125593 A1 | 8/2001 |
| EP | 1329233 B1 | 7/2003 |
| EP | 1350537 A1 | 10/2003 |
| EP | 1360970 A1 | 11/2003 |
| EP | 1380315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1475113 A1 | 11/2004 |
| EP | 1495775 A1 | 1/2005 |
| EP | 1502613 A1 | 2/2005 |
| EP | 1525873 A1 | 4/2005 |
| EP | 1527792 A1 | 5/2005 |
| EP | 1559442 A2 | 8/2005 |
| EP | 1616594 A1 | 1/2006 |
| EP | 1704889 A1 | 9/2006 |
| EP | 1719537 A2 | 11/2006 |
| EP | 1762259 A1 | 3/2007 |
| EP | 1764125 A1 | 3/2007 |
| EP | 1776980 A1 | 4/2007 |
| EP | 1970091 A1 | 9/2008 |
| EP | 2272559 A1 | 1/2011 |
| FR | 2725902 A1 | 10/1994 |
| FR | 2 752 164 A1 | 2/1998 |
| GB | 906574 | 9/1962 |
| GB | 2 088 215 A | 6/1982 |
| GB | 2 230 702 A | 10/1990 |
| GB | 2 423 267 A | 8/2006 |
| GB | 2 450 872 A | 7/2007 |
| GB | 2 459 101 A | 10/2009 |
| GB | 2459101 A | 10/2009 |
| JP | 10179734 A | 8/1991 |
| JP | 7051251 A | 11/1995 |
| JP | 8187286 A | 7/1996 |
| JP | 03-191965 A | 7/1998 |
| JP | 2002-028246 A | 1/2002 |
| RU | 2 238 111 C2 | 12/2003 |
| SU | 933 100 | 6/1982 |
| WO | WO 81/01795 A1 | 7/1981 |
| WO | WO 82/03558 A1 | 10/1982 |
| WO | WO 92/04062 A1 | 3/1992 |
| WO | WO 93/05840 A2 | 4/1993 |
| WO | WO 93/11709 A1 | 6/1993 |
| WO | WO 94/20160 A1 | 9/1994 |
| WO | WO 95/19194 A1 | 7/1995 |
| WO | WO 96/20021 A1 | 7/1996 |
| WO | WO 96/32981 A1 | 10/1996 |
| WO | WO 98/26835 A1 | 6/1998 |
| WO | WO 98/33549 A1 | 8/1998 |
| WO | WO 98/58693 A1 | 12/1998 |
| WO | WO 99/07435 A1 | 2/1999 |
| WO | WO 99/22789 A1 | 5/1999 |
| WO | WO 99/33504 A1 | 7/1999 |
| WO | WO 00/02614 A1 | 1/2000 |
| WO | WO 00/03757 A1 | 1/2000 |
| WO | WO 00/44324 A1 | 8/2000 |
| WO | WO 01/12746 A1 | 2/2001 |
| WO | WO 01/30419 A2 | 5/2001 |
| WO | WO 01/68180 A1 | 9/2001 |
| WO | WO 01/72353 A2 | 10/2001 |
| WO | WO 01/76684 A1 | 10/2001 |
| WO | WO 01/93926 A2 | 12/2001 |
| WO | WO 02/02165 A2 | 1/2002 |
| WO | WO 02/07804 A1 | 1/2002 |
| WO | WO 02/040083 A2 | 5/2002 |
| WO | WO 02/053220 A2 | 7/2002 |
| WO | WO 02/068014 A2 | 9/2002 |
| WO | WO 02/081012 A2 | 10/2002 |
| WO | WO 02/081013 A2 | 10/2002 |
| WO | WO 02/083206 A2 | 10/2002 |
| WO | WO 02/083228 A2 | 10/2002 |
| WO | WO-02083228 A2 | 10/2002 |
| WO | WO 02/094352 A2 | 11/2002 |
| WO | WO 02/100457 A2 | 12/2002 |
| WO | WO 02/102442 A1 | 12/2002 |
| WO | WO 03/015860 A1 | 2/2003 |
| WO | WO 03/026728 A1 | 4/2003 |
| WO | WO 03/068305 A1 | 8/2003 |
| WO | WO 03/075980 A2 | 9/2003 |
| WO | WO 03/095003 A1 | 11/2003 |
| WO | WO 2004/012796 A1 | 2/2004 |
| WO | WO 2004/024219 A1 | 3/2004 |
| WO | WO-2004024219 A1 | 3/2004 |
| WO | WO 2004/026375 A1 | 4/2004 |
| WO | WO 2004/029457 A1 | 4/2004 |
| WO | WO 2004/030726 A1 | 4/2004 |
| WO | WO 2004/056412 A2 | 4/2004 |
| WO | WO 2004/037325 A1 | 5/2004 |
| WO | WO 2004/054644 A1 | 7/2004 |
| WO | WO 2004/064593 A2 | 8/2004 |
| WO | WO 2004/071308 A1 | 8/2004 |
| WO | WO 2004/087240 A1 | 10/2004 |
| WO | WO 2004/098683 A1 | 11/2004 |
| WO | WO 2004/101016 A1 | 11/2004 |
| WO | WO 2004/101071 A2 | 11/2004 |
| WO | WO 2004/110527 A1 | 12/2004 |
| WO | WO 2005/002649 A1 | 1/2005 |
| WO | WO 2005/004973 A1 | 1/2005 |
| WO | WO 2005/018703 A2 | 3/2005 |
| WO | WO 2005/037184 A2 | 4/2005 |
| WO | WO 2005/037350 A2 | 4/2005 |
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/072795 A2 | 8/2005 |
| WO | WO 2005/092410 A1 | 10/2005 |
| WO | WO 2005/094920 A1 | 10/2005 |
| WO | WO 2005/112800 A2 | 12/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A2 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/062680 A1 | 6/2006 |
| WO | WO 2006/062912 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/120253 A2 | 11/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A2 | 1/2007 |
| WO | WO 2007/020090 A1 | 2/2007 |
| WO | WO 2007/065944 A1 | 6/2007 |
| WO | WO 2007/071255 A1 | 6/2007 |
| WO | WO-2007/071258 A1 | 6/2007 |
| WO | WO 2007/093051 A1 | 8/2007 |
| WO | WO 2007/093182 A2 | 8/2007 |
| WO | WO 2007/122207 A1 | 11/2007 |
| WO | WO 2007/140631 A1 | 12/2007 |
| WO | WO 2007/140783 A2 | 12/2007 |
| WO | WO 2007/140785 A1 | 12/2007 |
| WO | WO 2007/141210 A1 | 12/2007 |
| WO | WO 2008/014791 A1 | 2/2008 |
| WO | WO 2008/014792 A1 | 2/2008 |
| WO | WO 2008/133702 A1 | 3/2008 |

(56) References Cited

FOREIGN PATENT DOCUMENTS

| | | |
|---|---|---|
| WO | WO 2008/048631 A1 | 4/2008 |
| WO | WO 2008/052545 A1 | 5/2008 |
| WO | WO 2008/065646 A1 | 6/2008 |
| WO | WO 2008/092782 A1 | 8/2008 |
| WO | WO 2008/092958 A2 | 8/2008 |
| WO | WO 2008/092959 A1 | 8/2008 |
| WO | WO 2008/135098 A1 | 11/2008 |
| WO | WO 2008/147600 A1 | 12/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/016635 A2 | 2/2009 |
| WO | WO 2009/033032 A1 | 3/2009 |
| WO | WO 2009/039013 A1 | 3/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |
| WO | WO 2010/003885 A1 | 1/2010 |
| WO | WO 2010/003886 A1 | 1/2010 |
| WO | WO 2010/030602 A1 | 3/2010 |
| WO | WO 2010/034830 A1 | 4/2010 |
| WO | WO 2010/072664 A1 | 7/2010 |
| WO | WO 2010/080715 A1 | 7/2010 |
| WO | WO-2010080715 A1 | 7/2010 |
| WO | WO 2010/112521 A1 | 10/2010 |
| WO | WO 2011/012465 A1 | 2/2011 |
| WO | WO 2011/015659 A1 | 2/2011 |
| WO | WO 2011/121023 A1 | 10/2011 |
| WO | WO 2012/041784 A1 | 4/2012 |
| WO | WO 2012/041923 A2 | 4/2012 |
| WO | WO 2012/045667 A2 | 4/2012 |
| WO | WO 2012/107440 A1 | 8/2012 |

OTHER PUBLICATIONS

"Why inset®?" inset® infusion set product overview; downloaded from the internet at http://web.archive.org/web/20040906102448/http://www.infusion-set.com/Default.asp?ID=108 on Jan. 1, 2008; two pages.

International Application No. PCT/EP2011/067066 International Search Report and Written Opinion dated Jul. 6, 2012.

* cited by examiner

SPRINKLER CANNULA

This application claims the benefit under 35 U.S.C. § 371 of International Application No. PCT/EP2011/067066, filed Sep. 30, 2011, which claims the benefit of U.S. Provisional Application Ser. No. 61/389,595, filed Oct. 4, 2010 and European Application No. 10186437.9, filed Oct. 4, 2010, which are incorporated by reference herein in their entirety.

The present invention relates to an infusion device configured for introduction of a fluid drug into the human body. Specifically, the present invention relates to an infusion including a cannula configured for this purpose.

According to one aspect, the present invention relates to an infusion device including a cannula having a tubular body member with a proximal end and a subcutaneously placed distal portion having a distal end. The distal portion is provided with a radial opening allowing a portion of a drug conveyed through the tubular body member to discharge.

In general terms, an infusion device inter alia comprises following sub components:
  a hub like part comprising a body of hard material fastened to a patients skin via a mounting pad,
  a pump, and
  a cannula.

The proximal portion of a cannula is in this specification defined as a portion placed above the skin surface of the patient during use, and the distal portion of a cannula is in this specification defined as the portion which, after mounting, is placed subcutaneously i.e. below the skin surface of the patient. The distal end opening will normally be open allowing fluid to discharge, however according to certain applications and embodiments, the opening may be closed thereby increasing the fluid pressure on the radial opening or openings.

BACKGROUND

Hypodermic cannulas or needles have been used to introduce fluid drugs to the body of human beings as well as animals for over a century.

The use of these cannulas for this purpose has long been the method of last resort, especially for the injection of medications because of the pain associated with the forcing of the needle into the body. Over the years, manufacturers of these cannulas learned that the smaller the diameter of the cannula, and the sharper the point of the introducing needle, the more comfortable the injection would be, and as a consequence, it is today common practise to inject drugs by means of very fine cannulas.

There is, however, a limit to the degree to which the diameter of these cannulas may be reduced. One limitation is established by the flow rate of fluid drug along the cannula which is related to the fourth power of the diameter of the conduit. As the diameter is reduced, the flow rate, at similar pressure, rapidly decreases. If a certain volume of fluid is to be injected and the diameter of the conduit to be reduced, either the pressure used to move the fluid along within the cannula, or the time allotted for introducing the fluid, will increase.

Fluids such as insulin for treatment of diabetes are usually injected in the home by the patent. Such individuals may be unable to exert sufficient pressure to inject their insulin in a satisfactorily short period of time if the diameter of the cannula is too small.

One way to increase the flow rate of a fluid passing through a cannula is to place openings along the side of the needle. Such needles, known as sprinkler needles, are known in the art and are described, for example, by Gross in U.S. Pat. No. 6,261,272. The additional openings on the side of the needle provide additional access to the tissue creating a shorter fluid path to the tissue and also increasing the area of access to the tissue whereby the effective area of the outlet of the needle is increased. These advantages exist both in the delivery of the fluid to the tissue and in the extraction of fluid from the tissue.

A direct result of the sprinkler needle being able to deliver the fluid to a larger volume or area of tissue is a reduction of the pressure required to deliver the fluid. Further, and equally important, increasing the surface area of tissue exposed to the fluid enhances the absorption rate of the fluid by the body.

GB 2459101 A discloses a subcutaneous port and fenestrated catheter for the administration of fluids subcutaneously to be infused over a large volume of tissue. The port contains a subcutaneous chamber covered by a septum through which fluid is received from a hypodermic needle. The chamber has an exit hole with a nipple which connects to a catheter which has perforations. The port and catheter is implanted under the skin of the patient. According to the document, the port may have more than one exit hole connected to other catheters. GB 2459101 A is considered to represent relevant prior art with respect to the present invention because the reference is directed to frequent subcutanous infusion of a medicament by means of a cannula or catheter comprising one or more radial openings such that the fluid administered are received by a large tissue area.

US 2007/0129691 A disclose a laminated sprinkler needle for introduction and extraction of liquids from an animal. The needle comprising a substrate, a micro machined photo resistive layer and a micro porous layer. The structure is of simple construction and fabrication and, according to the document, provides higher flow rates than standard hollow cannulas.

While sprinkler needles have a performance advantage over straight cannula needles, this performance advantage comes at a significantly higher manufacturing cost. The additional openings must be cut in the sides of the needle which requires more time for manufacturing as well as additional manufacturing setups, and further, the openings must further be deburred in order to make sure the pain of insertion is low.

US 2005/0107743 A disclose an infusion set comprising a base member, an introducer cap and an infusion cap. The base member comprises a soft cannula extending from a lower side of the base member and a port on an upper side thereof. The port is configured to be in fluid communication with the soft cannula. The port also comprises a septum adapted to seal the port against unwanted fluid flow. The introducer cap is adapted to be mounted to the base member and has a needle adapted to extend through the septum and said soft cannula in an assembled position. The infusion cap comprises a lumen adapted to receive a flexible tube. The infusion cap also comprises a hard cannula adapted to be inserted through the septum and to place said soft cannula in fluid communication with said lumen. The soft cannula according to US 2005/0107743 A give rise to two problems, one being that the soft cannula is disposed for kinking and the another is that the soft cannula according to US 2005/0107743 A suffers from similar delivery restrictions as already mentioned above.

WO 2002/083228 A2 discloses a fairly advanced syringe or catheter system capable of injecting, manually or automatically; precisely measured quantities of liquids into a body. A plurality of needle designs is disclosed and according to the reference, the designs create advantageously shaped or diffused clouds, streams, or jets of medicament and the like. Generally, the reference seeks to set forth a syringe or catheter allowing for controlled injection of a medicament without substantial damage to tissue. According to the reference, the teachings of the reference may be applied to a relatively long and soft catheter or a rigid needle.

WO 2004/024219 A1 discloses a method and apparatus for epidermal or intradermal delivery of a medicament. A needle having at least one side port is used to penetrate the skin of a subject. The medicament is delivered through the side port and into the skin.

US 2010/0022956 A, by the applicant of the present invention, discloses an infusion set improvable by the teachings of the present application.

An infusion device comprising a cannula to be inserted by means of an insertion needle having following characteristics is much desired:
The cannula which is cheap and simple to manufacture,
The cannula which is user friendly and cause as little pain as possible to the end user, and
The cannula which is configured such that it will mitigate the effects of kinking.

BRIEF DESCRIPTION OF THE INVENTION

The present invention seeks generally to improve today's infusion devices such that the abovementioned insufficiencies and drawbacks of today's infusion devices are overcome.

Up to this day, prior art has failed to teach a simple and yet reliable and inexpensive infusion device which in a safe and reliable manner, without substantially increasing the cost of the device, is able to satisfy the abovementioned much desired characteristics of the mentioned infusion device.

According to the invention, there is provided an infusion device as per the introductory part of this specification, and in particular, upon configuring the infusion device such that the infusion device further comprise a hub part configured to be fastened onto an outside surface of a patients skin via a mounting pad, an infusion device resolving the abovementioned drawbacks are provided.

According to one embodiment, the infusion device may further include a pump configured to be in fluid connection with a reservoir configured to store or hold medication.

According to one embodiment, the subcutaneously placed distal portion may be made from soft material.

According to one embodiment, the cannula may be configured to be inserted by means of an insertion needle.

According to one embodiment the radial opening or openings may, when the cannula is inserted, be provided at least 1 millimeter below the skin surface.

According to one embodiment, the radial opening or openings may, when the cannula is inserted, be provided no more than 9 millimeter below the skin surface.

According to one embodiment, the radial opening may, when the cannula is inserted, be provided below the basal membrane.

According to one embodiment, the radial opening or openings may, when the cannula is inserted, be provided no more than 3 millimeter below the skin surface.

According to one embodiment, the cannula may further comprise a plurality of radial openings allowing a portion of a drug conveyed through the tubular body member to discharge.

According to one embodiment, the radial openings may be apportioned such that the radial openings extend only through one wall of the tubular body member. Further, the radial openings may or may not extend axially along a straight line along the tubular body member.

According to one embodiment, one or more radial openings may extend through the tubular body member in an angle lying approximately perpendicular to a longitudinal axis of the cannula.

According to one embodiment, one or more radial openings may extend through the tubular body member in at least one angle oriented different from an angle lying perpendicular to a longitudinal axis of the cannula.

According to one embodiment, the radial openings that may extend through the tubular body member may have substantially equal diameter.

According to one embodiment, the radial openings that may extend through the tubular body member may have varying diameter.

According to one embodiment, the radial openings which may have varying diameter may be arranged such that the opening having the largest diameter is arranged nearest the distal portion of the cannula.

According to one embodiment, the radial openings, which may have varying diameter, further may be arranged such that the radial opening having the smallest diameter is arranged nearest the proximal end of the cannula.

According to one embodiment, the length of the distal portion of the cannula may be less than 15 mm and the outer diameter of the distal portion may be less than 1.5 mm and the diameter of the one or more radial openings may be between 15 μm and 0.3 mm.

According to one embodiment, the infusion device may be configured for subcutaneous infusion of drugs such as insulin and the like.

DETAILED DESCRIPTION OF THE INVENTION WITH REFERENCE TO THE FIGURES

Figure 1:
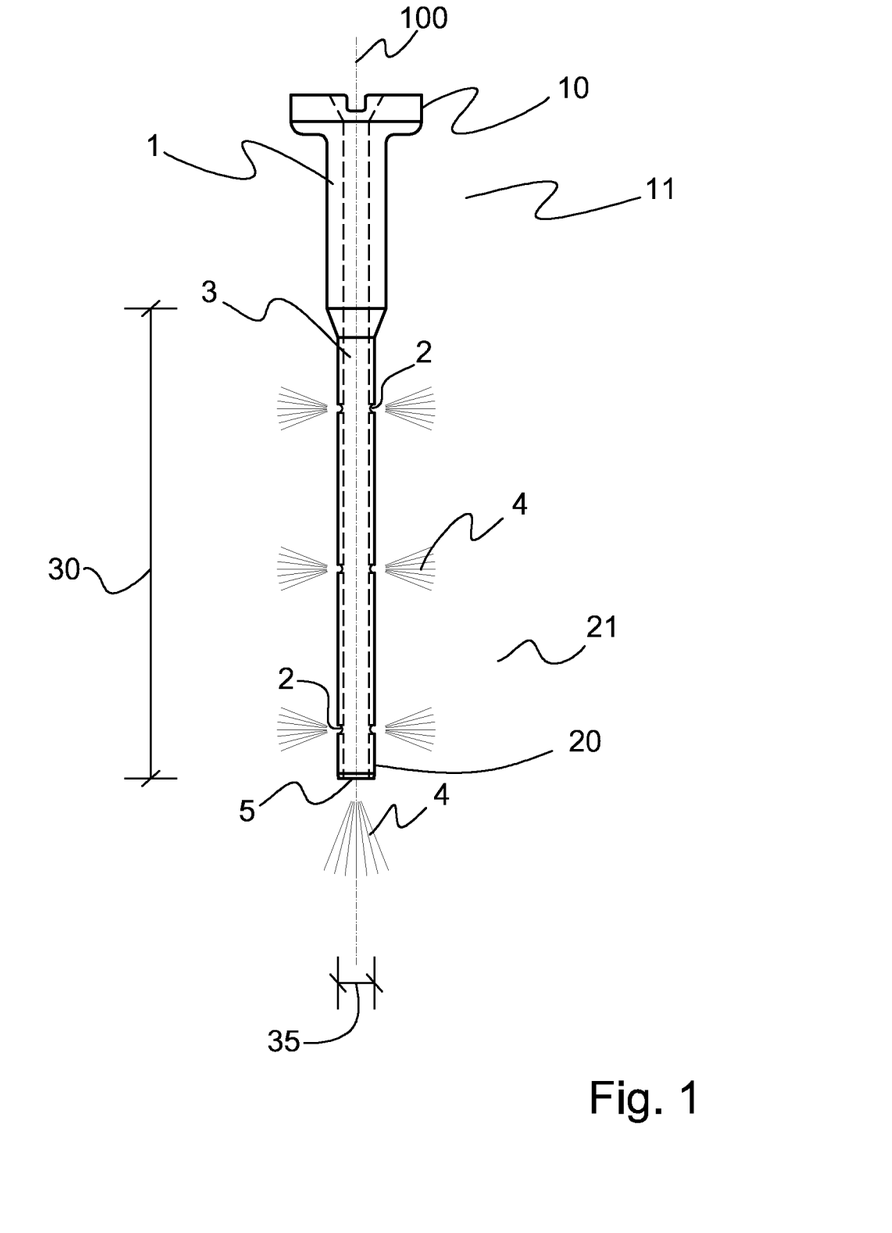
FIG. 1 is a plane view of an embodiment of a cannula applicable to the infusion device according to the present invention.

FIG. 1 shows a plane view of one embodiment of a cannula 1 applicable to an infusion device according to the present invention.

Figure 2:
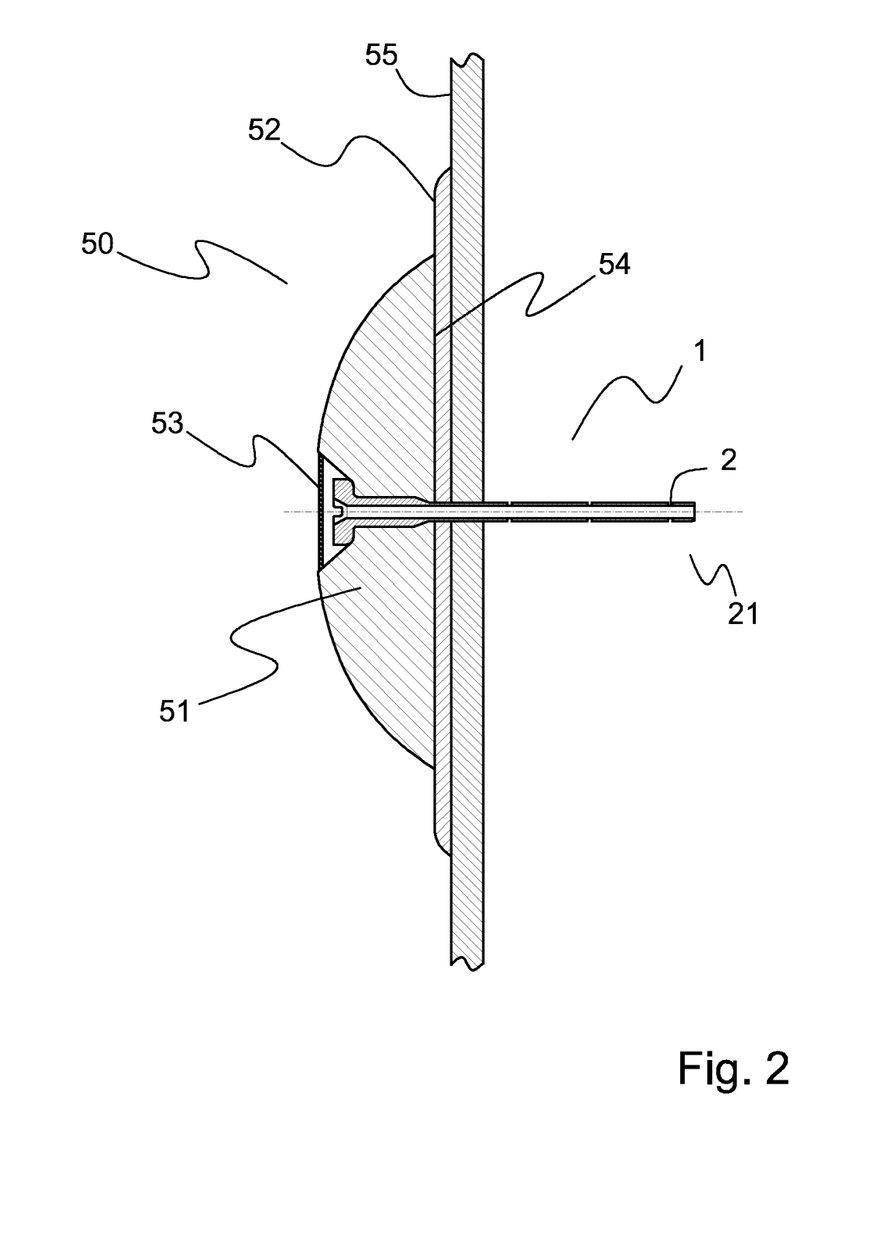
FIG. 2 is an infusion device according to the present invention.

The remaining parts and components of the infusion device is considered well known to those skilled in the relevant art, and therefore, such parts and components will only be briefly described in this specification, see FIG. 2.

Figure 3:
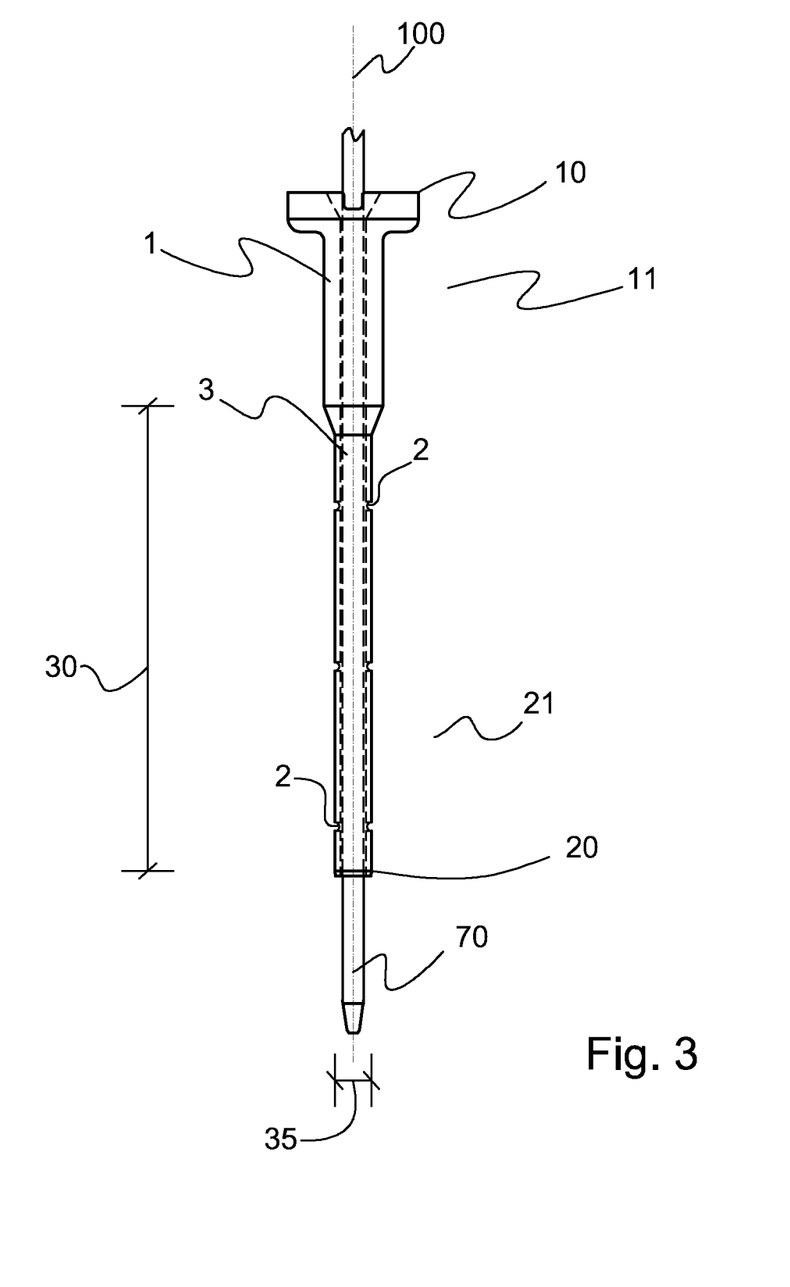
FIG. 3 is a plane view of a cannula applicable to the infusion device according to the present invention, here shown together with a part of an insertion needle.

As can be seen in FIG. 1 the cannula 1 is provided with a tubular body member 3 having a conduit shown by the dashed lines. The conduit interconnects the in this figure not shown infusion device with the openings 2 and 5. The cannula 1 includes a proximal end 10 configured for interconnection with the not shown infusion device as well as a distal portion 21 configured for subcutaneously placement by means of the insertion needle 70 shown in FIG. 3.

Numeral 5 refers to an outlet arranged in the distal portion 21, opposite the interconnection with the infusion device. The outlet 5 may or may not be considered the primary outlet for drugs 4. In addition to the outlet 5, the cannula 1 is provided with at least one further opening 2.

Figure 4:
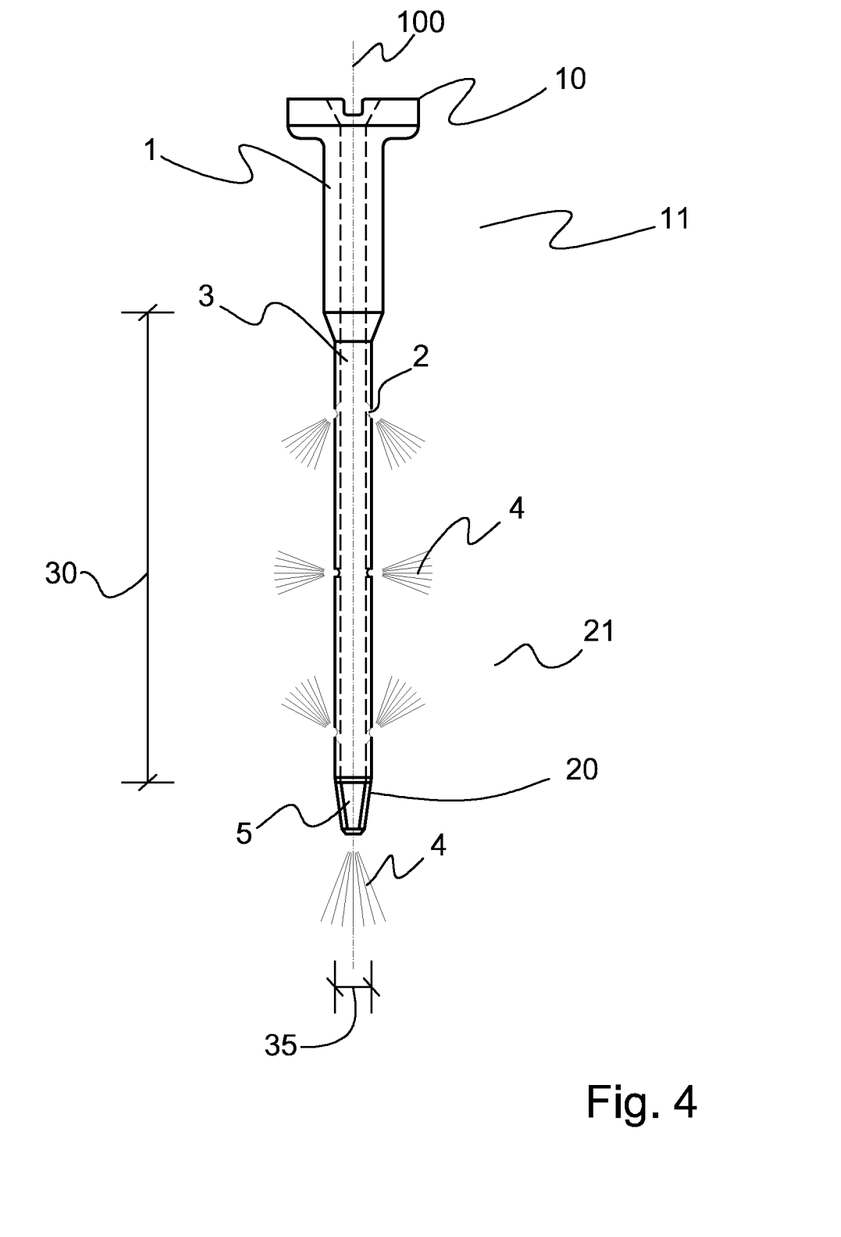
FIG. 4 is a plane view of an embodiment of a cannula applicable to the infusion device according to the present invention.
Figure 5:
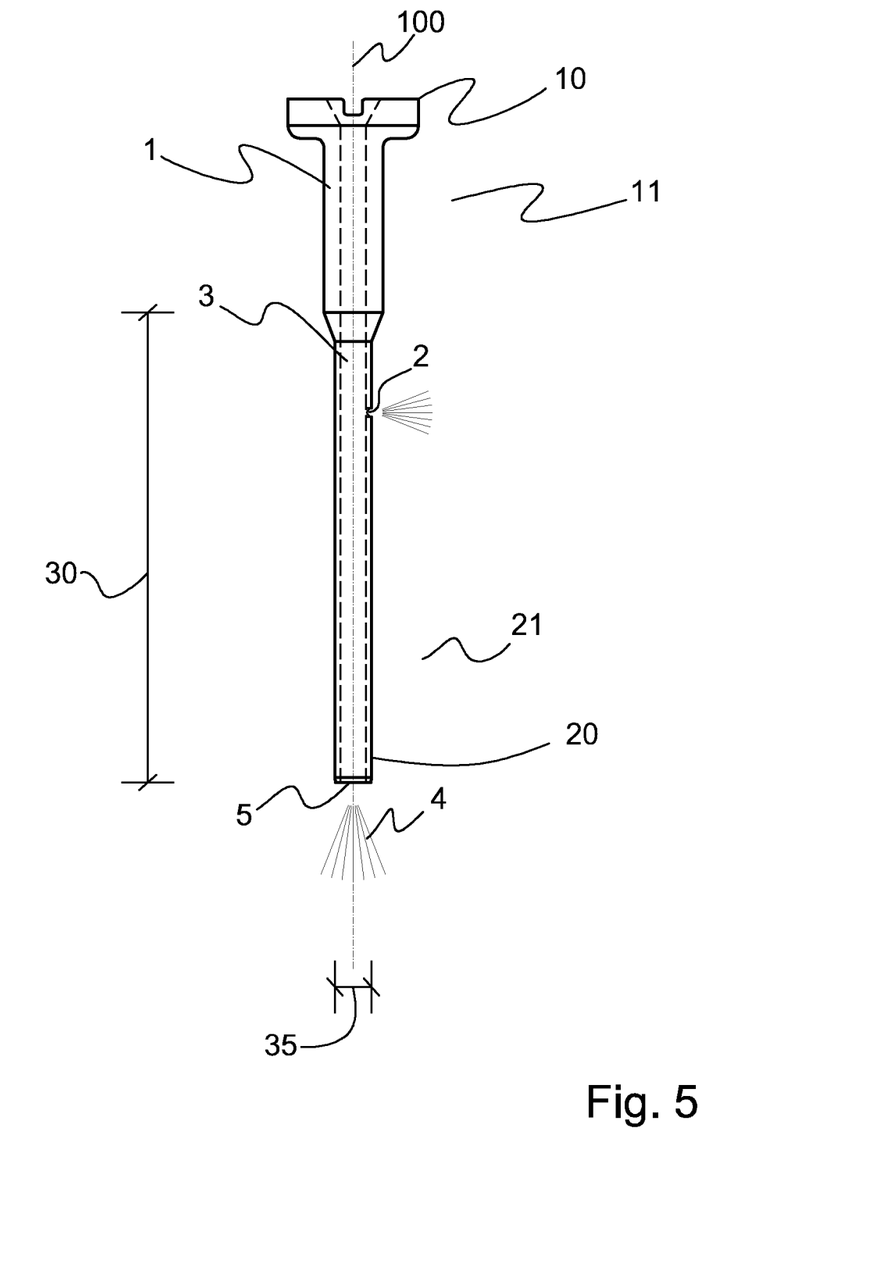
FIG. 5 is a plane view of an embodiment of a cannula applicable to the infusion device according to the present invention.

Although FIGS. 1-4 disclose the cannula 1 including a plurality of openings 2, the present invention is not in any way limited to embodiments of the cannula 1 comprising more than one opening 2, see FIG. 5.

The subcutaneously placed distal portion 21, alternatively the entire cannula 1, may be made from a soft material such as PTFE (Teflon), FEP, rubber, PE material or silicone base materials and the like.

At least one of the radial openings 2 may, when the cannula 1 is inserted, be provided at between 1 and 9 millimeter below the skin surface 55, see FIG. 2.

FIG. 2 illustrates schematically an infusion device according to the present invention. The infusion device 50 includes a cannula 1 having a tubular body member 3 with a proximal end 10 and a subcutaneously placed distal portion 21 having a distal end 20. The distal portion 21 of the cannula may be provided with a radial opening 2 allowing a portion of a drug 4 conveyed through the tubular body member 3 to discharge.

The infusion device according to FIG. 2 further include a hub part 51 configured to be fastened onto an outside surface of a patients skin 55 via a mounting pad 52. The mounting pad 52 may be provided with an adhesive layer, configured to adhere to a patient's skin, and a not shown removable release liner which covers the adhesive layer. The mounting pad 52 may be a dressing, a plaster, an adhesive pad or the like and the mounting pad may be configured in various shapes such as oval, circular, triangular rectangular etc.

According to one embodiment, the infusion device may include a hub part 51 having a main plane being essentially parallel to the skin of the patient, when the infusion set is attached to a patient. The hub part 51 may have a main 54 surface being closest to the skin of a patient, and the main surface may be provided with fastening means such as the mounting pad 52 for fastening the infusion device to the skin 55 of a patient.

In the embodiment according to FIG. 2, the cannula 1 extends from the hub part 51 through the fastening means or mounting pad 52. Alternatively the cannula 1 may extend from the hub part 51 of the infusion device essentially along an inclined axis of insertion (not shown).

As shown in FIG. 2, the hub part 51 may include a septum or barrier 53.

As can be seen in FIGS. 1-4, the cannula 1 may be provided with a plurality of radial openings 2 allowing the drug 4, conveyed through the tubular body member or hollow 3, to discharge. The openings 2 may be apportioned such that the openings 2 extend through one wall of the tubular body member 3 only, see FIG. 4. Further, the radial openings 2 may extend axially along a not shown straight line along the cannula 1. The radial openings 2 may, in other embodiments, be placed on different quarters of the cannula 1 such that all the holes are not blocked when pressure is applied to one side of the cannula 1.

The opening or openings 2 may or may not extend through said tubular body member in an angle lying approximately perpendicular to a longitudinal axis of the cannula 1. Further, the opening or openings 2 may extend through the tubular body member in at least one angle oriented different from an angle lying perpendicular to the longitudinal axis 100 of the cannula 1, as shown in FIG. 4.

The angles may constitute any angle between 0° and 180° relative to the longitudinal axis 100; however angles lying in-between 30° and 150°, alternatively 60° and 120° or even 90° may be preferred.

The radial opening or openings 2 may have substantially equal diameter, although this is not in any way a requirement of the present invention. The opening or openings 2 may, according to certain embodiments, also have varying diameter.

It may be preferred to apply the radial opening or openings 2 as a spherical opening or openings; however other forms of opening or openings may equally be applied as long as the opening or openings do not adversely affect the strength and functionality of the cannula 1.

In case the cannula is provided with radial openings 2 having varying diameter, the openings 2 may be arranged such that the opening 2 having the largest diameter is arranged nearest the distal portion 21 of the cannula 1, whereby a substantially uniform outlet of fluid may be obtained over the length of the cannulas distal portion 21.

The length 30 of the distal portion 21 of the cannula 1 may be less than 30 mm, preferably 15 mm, and the outer diameter 35 of the distal portion 20 may be less that 2 mm, preferably less than 1.5 mm and the diameter of the opening or openings 2 may be between 10 µm and 0.5 mm, preferably between 25 µm and 0.3 mm.

The distal end 20 of the cannula 1 may or may not be tapered such as shown in FIG. 4. Providing the distal end 20 of the cannula 1 with a tapered end may facilitate insertion of the cannula 1. Although only the embodiment according to FIG. 4 is shown with a slant and tapered end, this may not in any way be considered limiting to other embodiments according to this specification.

Figure 6:
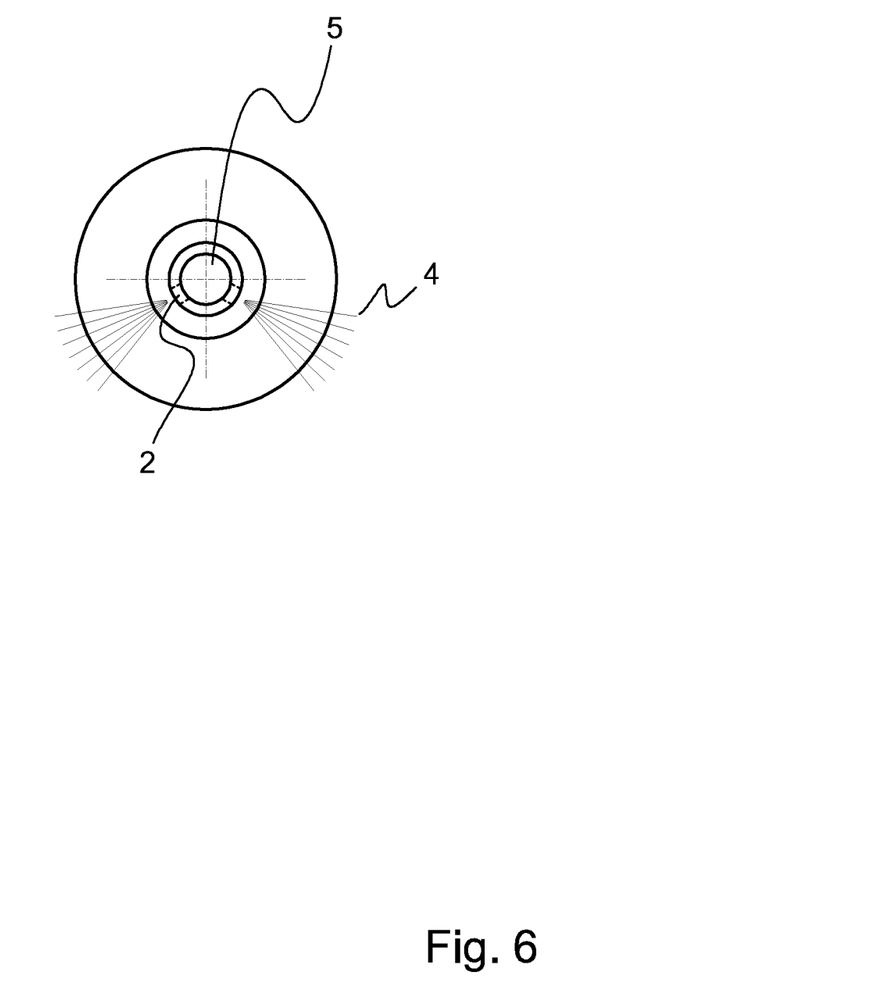
FIG. 6 is an end view of an embodiment of a cannula applicable to the infusion device according to the present invention.

The number of radial openings may, as already mentioned, vary from only one, such as shown in FIG. 5, to any number of openings, however according to one preferred embodiment, the cannula is provided with two radial openings, such as shown in the end view according to FIG. 6.

According to a well functioning embodiment, the cannula may be provided with two radial openings, or sprinkler holes, which are not located opposite each other, i.e. the openings are offset longitudinally as well as with respect to an angle seen from the end or circular cross section. A well functioning angle between the opening are considered to be 120 degree, see FIG. 6.

The opening or openings may be provided, by means of drilling, punching, cutting or equivalent, in any angle to the longitudinal axis 100 of the cannula 1.

Generally seen, the cannula for the infusion device according to the present invention allows a drug such as insulin to be absorbed faster in the blood of the patient than the "one-outlet" soft cannulas according to today's infusion devices comprising cannulas made from a soft material.

According to certain aspects of the present invention, it has been found that one or more radial openings reduce soft cannulas well known tendency to occlude, e.g. due to kinking. Hence the cannula for the infusion device according to the present invention is less inclined to malfunction as a result of kinking.

The application and combination of features and solutions presented by the present invention is not limited to the presented embodiments. One or more features of one embodiment can and may be combined with one or more not disclosed features of other embodiments, whereby not described, but valid, embodiments of the present invention may be obtained. One example is that the cannula according to the present invention may form part of an infusion device provided with means for monitoring or asserting whether or not the cannula of the infusion set is inserted as intended. Such means could inter alia constitute means configured for measuring impedance, where one option of performing the measurement by means of measuring impedance could be by using a drug such as insulin present in the cannula as an electrode.

The term "comprises/comprising/comprised of" when used in this specification incl. claims is taken to specify the presence of stated features, integers, steps or components but does not preclude the presence or addition of one or more other features, integers, steps, components or groups thereof.

The invention claimed is:

1. An infusion device configured for subcutaneous placement by an insertion needle and infusion of a drug comprising:
    a cannula having a tubular body member, defining a conduit, with a proximal end and a subcutaneously placed distal portion having a wall and a distal end, wherein said distal portion comprises a soft material, wherein the soft material comprises a material selected from PTFE, FEP, rubber, PE material or silicone base materials, and wherein said distal portion further comprises at least two radial openings along the wall of the distal portion and an outlet at the distal end allowing a portion of the drug conveyed through said tubular body member to discharge into subcutaneous tissue of a patient, wherein the at least two radial openings discharge the drug towards the distal end of the cannula, and wherein the at least two radial openings along the wall of the distal portion have a diameter between 10 μm and 0.5 mm and the outlet at the distal end has an outer diameter of less than 1.5 mm, and wherein two of the at least two radial openings are not located opposite each other including where the two radial openings are offset from each other along a longitudinal axis, and with respect to an angle seen from the outlet;
    wherein a length of said distal portion of said cannula is less than 15 mm and the length permits a portion of the insertion needle to extend past the outlet of the distal end during placement of the infusion device;
    a hub part configured to be fastened onto an outside surface of a patient's skin via a mounting pad, wherein the at least two radial openings reduce occlusion due to kinking of the cannula;
    wherein the outlet of said cannula is tapered to facilitate insertion of the cannula with the insertion needle and the angle between two of the at least two radial openings is substantially 120 degrees.

2. The infusion device according to claim 1, wherein said at least two radial openings are positioned at least 1 millimeter below the skin surface when said cannula is subcutaneously placed.

3. The infusion device according to claim 1, wherein said at least two radial openings are positioned no more than 9 millimeters below the skin surface when said cannula is subcutaneously placed.

4. The infusion device according to claim 1, wherein said at least two radial openings are positioned below the basal membrane when said cannula is subcutaneously placed.

5. The infusion device according to claim 1, wherein said at least two radial openings are positioned no more than 3 millimeters below the skin surface when said cannula is subcutaneously placed.

6. The infusion device according to claim 1, wherein said device further comprises a pump in fluid connection with a reservoir configured to store medication.

7. The infusion device according to claim 1, wherein said infusion device is configured for subcutaneous infusion of one or more drugs.

8. The infusion device according to claim 7, wherein said one or more drugs comprise insulin.

9. The infusion device according to claim 1 wherein the at least two radial openings include a first radial opening inclined with respect to the longitudinal axis and toward the outlet, a second radial opening substantially perpendicular to the longitudinal axis, and a third radial opening inclined with respect to the longitudinal axis and away from the outlet.

10. The infusion device according to claim 1, wherein the infusion device comprises three or more radial openings.

11. The infusion device according to claim 10, wherein said plurality of radial openings extending through said tubular body member have substantially equal diameter.

12. The infusion device according to claim 10, wherein said plurality of radial openings extending through said tubular body member have varying diameters.

13. The infusion device according to claim 12, wherein said plurality of radial openings having varying diameters are configured such that the radial opening having a smallest diameter is arranged nearest said distal portion of said cannula.

14. The infusion device according to claim 12, wherein said plurality of radial openings having varying diameters are configured such that the radial opening having a smallest diameter is arranged nearest said proximal end of said cannula.

* * * * *